United States Patent
Pöchlauer et al.

Patent Number: 5,929,251
Date of Patent: Jul. 27, 1999

[54] PROCESS FOR THE PREPARATION OF CARBOXYLIC ACID SUCCINIMIDYL ESTERS

[75] Inventors: Peter Pöchlauer, Puchenau; Wolfram Hendel; Christian Burger, both of Leonding; Anita Lamplmayr, Linz; Harald Pöschko, Ennsdorf; Antonia Praus; Gerald Summer, both of Linz, all of Austria

[73] Assignee: DSM Fine Chemicals Austria GmbH, Australia

[21] Appl. No.: 09/000,565

[22] Filed: Dec. 30, 1997

Related U.S. Application Data

[62] Division of application No. 08/833,120, Apr. 4, 1997, Pat. No. 5,734,064.

[30] Foreign Application Priority Data

Apr. 4, 1996 [AT] Austria ........................... 609/96

[51] Int. Cl.$^6$ ................................. C07D 207/12
[52] U.S. Cl. ............................................. 548/547
[58] Field of Search ............................................. 548/547

[56] References Cited

U.S. PATENT DOCUMENTS

| | | | |
|---|---|---|---|
| 4,341,707 | 7/1982 | Ogura et al. | 260/326 |
| 5,459,131 | 10/1995 | Albright et al. | 514/19 |
| 5,734,064 | 3/1998 | Pochlauer et al. | 548/542 |

*Primary Examiner*—Robert W. Ramsuer
*Assistant Examiner*—Dominic Keating
*Attorney, Agent, or Firm*—Wenderoth, Lind & Ponack LLP

[57] ABSTRACT

Process for the preparation of carboxylic acid succinimidyl esters by reaction of N-hydroxysuccinimide with a carboxylic acid and a halophosphoric acid ester of the formula

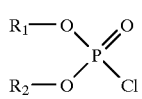

I in which $R_1$ and $R_2$ are identical or different and are a $C_2$- to $C_6$-alkyl radical or a phenyl radical, or $R_1$ and $R_2$ together form a $C_6$-aryl radical, in the presence of a base in a diluent at a temperature of 0° C. up to 100° C. and isolation of the corresponding carboxylic acid succinimidyl ester.

2 Claims, No Drawings

PROCESS FOR THE PREPARATION OF CARBOXYLIC ACID SUCCINIMIDYL ESTERS

This is a divisional of Ser. No. 08/833,120, filed Apr. 4, 1997, now U.S. Pat. No. 5,734,064.

Sucinimidyl esters are used, inter alia, as activated acyl derivatives, in particular when other acylating agents, such as acid chlorides or anhydrides, cannot be employed on account of the lability of starting materials or final products. This applies particularly in the field of peptide chemistry. For coupling a covalent peptide bond, an activated carboxyl component is necessary. The previously most frequently used method for carboxyl activation is based on the formation of succinimidyl esters by reaction of the corresponding carboxylic acid with carbodiimides, such as, for example, N,N'-dicyclohexylcarbodiimide (DCC) and N-hydroxysuccinimide. The disadvantage in this process lies, on the one hand, in the coupling reagent DCC on account of its allergenicity and of the high price, and, on the other hand, in the by-product N,N'-dicyclohexylurea obtained here, which firstly contaminates the succinimidyl ester and secondly has to be disposed of. For these reasons, it was attempted to replace the system DCC/N-hydroxysuccinimide. Possible alternatives are systems of the type halophosphoric acid ester/N-hydroxysuccinimide/base.

Tetrahedron Letters Vol. 21, pp. 1467–1468, [1980] and Chemical Abstracts Vol. 95: 203746 disclose a process for the preparation of diphenylsuccinimidoyl phosphate (SDPP) in which diphenyl chlorophosphate is reacted at room temperature with hydroxysuccinimide in an aqueous or organic solution, for example in methylene chloride, under the reaction conditions for Schotten-Baumann reactions. SDPP is isolated, optionally recrystallized and then reacted with a Z- or Boc-protected amino acid in the presence of a base and of acetonitrile to give the corresponding amino acid succinimidyl ester, which is used as an activated carboxyl component for peptide couplings.

J. Org. Chem., Vol. 47, No 15, [1982], page 2985 discloses an improved process, compared to the abovementioned process, for the preparation of SDPP in which SDPP is prepared under even more careful conditions, namely with cooling by means of an ice/salt solution.

The object of the present invention was to find a process for the preparation of succinmidyl esters, which leads in a simple manner and without isolation of SDPP to higher total yields of the desired succinimidyl esters and is applicable to a multiplicity of carboxylic acids.

Unexpectedly, it was possible to achieve this object by means of a process in which the reaction to give the carboxylic acid succinimidyl esters is carried out as a one-pot reaction and at temperatures of up to 100° C., it being possible for the addition of the reactants to be carried out in any desired sequence.

The present invention accordingly relates to a process for the preparation of carboxylic acid succinimidyl esters, which comprises reacting N-hydroxysuccinimide with a carboxylic acid and a halophosphoric acid ester of the formula

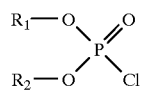
I in which $R_1$ and $R_2$ are identical or different and are a $C_2$- to $C_6$-alkyl radical or a phenyl radical, or $R_1$ and $R_2$ together form a $C_6$-aryl radical, in the presence of a base in a diluent at a temperature of 0° C. up to 100° C. and isolating the corresponding carboxylic acid succinimidyl ester.

The process according to the invention is suitable for the preparation of succinimidyl esters of carboxylic acids. Carboxylic acids are in this case understood as meaning all compounds of the general formula

II which form a succinimidyl ester which is stable under the reaction conditions according to the invention.

Of particular importance here are succinimidyl esters of N-substituted amino acids.

In the formula II, the radical A can be a saturated or mono- or polyunsaturated, linear, branched or cyclic alkyl group, an aryl group, an arylalkyl group or a heterocyclic group.

The radical A can be either unsubstituted or mono- or polysubstituted by groups which are inert under the reaction conditions. Possible substituents are, for example, halogen, such as chlorine or bromine, hydroxyl groups, nitro groups $(C_1–C_4)$-alkyl groups, $(C_1$–to $C_4)$-alkoxy groups, oxo groups, ester groups or secondary or tertiary amine groups. Furthermore, the compounds can additional contain a second carboxyl group such that the formation of disuccinimidyl esters occurs.

Examples of suitable carboxylic acids are:

linear, branched or cyclic, aliphatic, saturated, unsubstituted mono- or dicarboxylic acids having 2 to 60 C atoms, such as, for example, acetic acid, propionic acid, butyric acid, isobutyric acid, valeric acid, isovaleric acid, trimethylacetic acid, ethylmethylacetic acid, caproic acid, caprylic acid, capric acid, lauric acid, palmitic acid, stearic acid, pivalic acid, n-hexacosanoic acid, malonic acid, succinic acid, glutaric acid, adipic acid, pimelic acid, suberic acid, azelaic acid, sebacic acid, linear or branched, aliphatic, mono- or poly-unsaturated, unsubstituted mono- or dicarboxylic acids having 2 to 20 C atoms, such as, for example, acrylic acid, methacrylic acid, crotonic acid, isocrotonic acid, vinylacetic acid, oloic acid, sorbic acid, linoleic acid, linolenic acid, maleic acid, fumaric acid, acetylenedicarboxylic acid, hexinedioic acid, hexenedioic acid, unsubstituted, aromatic or aliphatic mono- or dicarboxylic acids having 7 to 20 C atoms, such as, for example, benzoic acid, phenylacetic acid, cinnamic acid, phthalic acid, isophthalic acid, terephthalic acid, 1- or 2-naphthalenecarboxylic acid, 1,5-naphthalenedicarboxylic acid or unsubstituted heterocyclic mono- or dicarboxylic acids such as, for example, 4-pyridinecarboxylic acid, 2,3-pyridinedicarboxylic acid, quinaldic acid.

Substituted carboxylic acids are, for example halocarboxylic acids, such as, for example, monochloroacetic acid, chloropropionic acid, dichloroacetic acid, trichloroacetic acid, chlorovaleric acid, hydroxycarboxylic acids such as, for example, lactic acid, γ-hydroxyvaleric acid, glycolic acid, racemic acid, salicylic acid, gallic acid, p-cumaric acid, caffeic acid, mandelic acid, oxocarboxylic acids such as, for example, glyoxylic acid, pyruvic acid, acetoacetic acid, levulinic acid, pulvinic acid, E-9-oxo-2-decenoic acid, N-substituted amino acids, such as, for example, Z-phenylalanine, Z-aspartic acid β-benzyl ester, N-phenylglycine, Z-valine, N-(1-ethoxycarbonyl-3- phenylpropyl)alanine, and further carboxylic acids substituted by $NO_2$, sec- or tert-amine groups, ester groups ($C_1$ to $C_4$)-alkyl or alkoxy groups, for example nitrobenzoic acid, acetylsalicylic acid, toluic acid, etc.

In the process according to the invention, the appropriate carboxylic acid is reacted with N-hydroxysuccinimide and a halophosphoric acid ester of the formula I in the presence of a base. Suitable halophosphoric acid esters are compounds of the formula I in which $R_1$ and R2 are identical or different and are a $C_2$- to $C_6$-alkyl radical or a phenyl radical, or $R_1$ and R2 together form a $C_6$-aryl radical. Examples of these are diphenyl chlorophosphate, diethyl chlorophosphate, dibutyl chlorophosphate and resorcinyl chlorophosphate. Preferably, diphenyl or dibutyl chlorophosphate is employed, particularly preferably diphenyl chlorophosphate.

Suitable bases for the reaction are carbonates such as, for example, sodium carbonate, sodium hydrogen-carbonate, potassium carbonate, etc., hydroxides, such as, for example, sodium hydroxide, potassium hydroxide, etc., or amines such as, for example, triethylamine, N-methylpyrrolidone, N-methyl- or N-ethylmorpholine etc.

In the reaction, the sequence of addition of the individual reaction components can be varied in any desired manner. Thus, for example, only one or two of the reaction components can be initially introduced into a diluent first. The base here can either be initially introduced at the same time as these compounds, but also subsequently metered into the initial charge. Lastly, the addition of the still lacking reactants, preferably in the diluent which is also used as the initial charge, is carried out in any desired sequence. For example, however, the base can also firstly be initially introduced in a suitable diluent, then N-hydroxysuccinimide and the halophosphoric acid ester can be added with stirring, and subsequently thereto the appropriate carboxylic acid can be admixed in a diluent which is also used as the initial charge. However, the base, N-hydroxysuccinimide and the carboxylic acid can also firstly be introduced into the initial charge and subsequently thereto the halophosphoric acid ester, in turn preferably in the diluent which is also used as the initial charge, can be added to the reaction mixture.

The reaction is preferably carried out with equivalent amounts of the reactants; an excess of N-hydroxysuccinimide, halophosphoric acid ester and/or base may be helpful. Per mole of carboxyl group, preferably 1 to 2 mol, particularly preferably 1 to 1.5 mol, of N-hydroxysuccinimide, preferably 1 to 2 mol, particularly preferably 1 to 1.5 mol, of halophosphoric acid ester and preferably 2 to 5 mol, particularly preferably 2 to 4 mol, of base are thus added. Larger amounts of N-hydroxysuccinimide, base or halophosphoric acid ester can also be employed if desired.

Diluents which can be used are both organic diluents which are hardly miscible or immiscible with water, such as, for example, ethyl acetate, methylene chloride, methyl tert-butyl ether etc., and organic diluents which are miscible with water, such as, for example, acetone, acetonitrile, tetrahydrofuran, dimethoxyethane etc. If a diluent which is miscible with water is employed, a water/diluent mixture can optionally also be used. The choice of the solvent is in this case dependent on the properties of the reactants employed and of the desired final product.

The reaction temperature can be 0° C. to 100° C. Preferably, the reaction temperature is between 10 and 80° C., particularly preferably between 20 and 60° C. Lower temperatures can also be set if desired; however, the reaction then proceeds more slowly. In the reaction, an increase in the temperature of the reaction mixture can occur, however, the desired reaction temperature can also be set by external energy supply.

Depending on the chemical structure of the carboxylic acids employed in each case, the reaction mixture thus obtained is kept at the reaction temperature for a few minutes up to several hours to complete the reaction. The reaction mixture, if necessary, is then cooled, preferably to about 15 to 30° C., and the carboxylic acid succinimidyl ester is isolated if desired.

The isolation of the carboxylic acid succinimidyl ester obtained by the process above can vary depending on the properties of the succinimidyl ester. If the reaction was carried out in a diluent which is immiscible or hardly miscible with water, the reaction mixture obtained by the process according to the invention can be treated with water to remove salts, whereupon phase separation occurs and the corresponding carboxylic acid succinimidyl ester is isolated from the organic phase. To isolate the ester from the organic phase, this is separated from the aqueous phase in a customary manner, washed and optionally dried, then the diluent is removed, for example by distillation, optionally under reduced pressure.

If a diluent which is miscible with water was used for the reaction, then the diluent must first be removed. The residue which remains is then treated with a mixture of water and a diluent which is immiscible or hardly miscible with water, whereupon phase separation occurs and the easter is isolated from the organic phase as described above. Alternatively, by adding a suitable diluent, for example an aqueous solution of an inorganic salt, for example sodium chloride or sodium sulfate, a phase separation and thus a separation of the succinimidyl ester from by-products can be brought about.

The crude product thus obtained, if desired, can additionally be purified by customary processes such as, for example, recrystallization and chromatography. In a further isolation variant, for example, the reaction mixture obtained after the reaction is evaporated and the residue is taken up in a suitable diluent, such as, for example, ethanol, the other reaction products going into solution and the carboxylic acid succinimidyl ester remaining as a solid. The succinimidyl ester is then filtered off and washed or recrystallized and dried.

The reaction mixture obtained by the process according to the invention, however, can also be reused for a subsequent reaction, for example for a peptide coupling reaction or for other acylation reactions with suitable nucleophiles, without working up or isolation of the carboxylic acid succinimidyl ester. Thus, for example, the organic phase containing the carboxylic acid succinimidyl ester can be employed directly, after separation of the aqueous phase containing the other reaction products, for the next step without prior work up. Depending on the particular subsequent reaction, to do this, if appropriate, the diluent of the organic phase is removed, and the unpurified carboxylic acid succinimidyl ester is dissolved in a diluent suitable for the respective subsequent reaction and reacted with an appropriate nucleophile, for example with an amino acid, an amino acid derivative or an amino, whereupon the desired subsequent product is isolated from the reaction mixture. The reaction parameters to be set are dependent on the chosen subsequent reaction in each case and can therefore vary within wide ranges.

Preferably, the subsequent reaction carried out is a peptide coupling. In this case, the carboxylic acid succinimidyl ester is coupled to the amino group of an amino acid or an amino acid derivative with elimination of N-hydroxysuccinimide to give the corresponding peptide.

By means of the process according to the invention, carboxylic acid succinimidyl esters and their subsequent products are obtained in a simple one-pot reaction in high yields and in excellent purity.

EXAMPLE 1

3.45 g (0.041 mol) of sodium hydrogencarbonate, 0.10 g of $H_2O$ and 30 ml of acetone were initially introduced into a 3-necked round-bottomed flask having a dropping funnel, thermometer and KPG stirrer and having a condenser with a delivery tube. 2.79 g (0.010 mol) of (S,S)-N-(1-ethoxycarbonyl-3-phenylpropyl)alanine (ECPA) and 1.20 g (0.010 mol) of N-hydroxysuccinimide were then added and the reaction mixture was heated to 50° C. 3.22 g (0.012 mol) of diphenyl chlorophosphate were then added dropwise in the course of 10 minutes and the reaction mixture thus obtained was stirred at 50° C. for 1 hour. Subsequently thereto, it was cooled to 20° C. in a water bath and the acetone was stripped off in a water-jet vacuum via the reflux condenser in the reaction flask. 30 ml of ethyl acetate and 30 ml of H2O were then added to the residue. After phase separation had been carried out in a separatory funnel, the organic phase was extracted with 30 ml of $NaHCO_3$ solution, dried with $Na_2SO_4$ p.a. and concentrated in a rotary evaporator at 40° C. and 20 mbar.

Yield of ECPA succinimidyl ester: 3.25 g (86.3% of theory)

EXAMPLE 2

1.4 g (0.012 mol) of N-hydroxysuccinimide, 3.5 g (0.041 mol) of sodium hydrogencarbonate and 10 ml of ethyl acetate were initially introduced. 3.8 g (0.014 mol) of diphenyl chlorophosphate in 10 ml of ethyl acetate were then added dropwise. A suspension of 2.8 g (0.010 mol) of ECPA in 30 ml of ethyl acetate was then added at 50° C. and the mixture was stirred at room temperature for 1.5 hours. 30 ml of dist. $H_2O$ were then added to the reaction mixture thus obtained, whereupon a phase separation took place. The organic phase was then extracted once with 30 ml of sodium hydrogencarbonate, dried and concentrated in a rotary evaporator at about 50° C. and 20 mbar.

Yield of ECPA succinimidyl ester: 3.0 g (80% of theory)

EXAMPLE 3

2.42 g (0.021 mol) of N-hydroxysuccinimide and 5.06 g (0.050 mol) of triethylamine were initially introduced into 5 ml of ethyl acetate and the suspension was stirred at room temperature. 2.72 g (0.020 mol) of solid 4-toluic acid were added to this suspension in the course of 5 min. and then a solution of 5.64 g (0.21 mol) of diphenyl chlorophosphate was added dropwise in the course of 20 min., the reaction mixture warming to about 35° C. The mixture was stirred at room temperature for 1 hour until the reaction was complete. The reaction mixture was then diluted with 100 ml of ethyl acetate and the organic phase was washed with 50 ml each of water, 2N hydrochloric acid and 10% strength aqueous sodium hydrogencarbonate solution and then evaporated. 4.65 g of crude product were isolated, which was then stirred at room temperature for 30 minutes with 20 ml of methyl tert-butyl ether. The white crystalline solid was filtered off and dried at 50° C. and 10 mbar. 4.28 g (94%) of 4-toluic acid succinimidyl ester were isolated.

M.p.: 176–180° C. (dec.)

EXAMPLE 4

1.73 g (0.010 mol) of quinaldic acid were initially introduced into 30 ml of acetone and 1.27 g (0.011 mol) of solid N-hydroxysuccinimide were added. A solution of 2.53 g (0.025 mol) of triethylamine in 10 ml of acetone was then added to this suspension in the course of 5 min. and the mixture was stirred at room temperature. After 30 min., a solution of 3.22 g (0.012 mol) of diphenyl chlorophosphate in 10 ml of acetone was added dropwise in the course of 10 min., the solution turning red with slight warming and salts precipitating. The mixture was stirred at room temperature for 20 hours until the reaction was complete. The suspension thus obtained was evaporated, the residue was taken up in 50 ml of ethanol and the solution was stirred at room temperature for 1 hour. The solid was then filtered off, washed with 2×3 ml of ethanol and dried for 1 hour at 1 mbar. 2.45 g (91%) of a pink-colored powder of quinaldic acid succinimidyl ester were obtained.

M.p.: 193–196° C. (dec.)

EXAMPLE 5

1.38 g (0.012 mol) of N-hydroxysuccinimide and 3.36 g (0.040 mol) of sodium hydrogencarbonate were initially introduced into 10 ml of acetonitrile and the mixture was stirred at room temperature. A solution of 1.73 g (0.010 mol) of quinaldic acid in 80 ml of acetonitrile and a solution of 3.22 g (0.012 mol) of diphenyl chlorophosphate in 10 ml of acetonitrile were then added in the course of 30 min. The pink-colored suspension obtained was stirred at room temperature for 16 hours and then warmed to 40° C. in a water bath for a further 24 hours. After ending of the reaction, the reaction mixture was evaporated in vacuo and the residue was taken up in 50 ml of dichloromethane. The suspension was filtered and the filter residue was washed with 2×20 ml of dichloromethane. The combined filtrates were washed with 100 ml each of water, 5% strength aqueous $NaHCO_3$ solution and water again. After evaporating the organic phase, 2.0 g of crude product were obtained. This was reprecipitated in a mixture of 30 ml of dichloromethane and 150 ml of n-hexane. The precipitate was filtered, washed with 5 ml of n-hexane and dried in vacuo. 1.9 g (70%) of a beige solid of quinaldic acid succinimidyl ester were obtained.

M.p.: 191–196° C. (dec.)

EXAMPLE 6

1.73 g (0.010 mol) of quinaldic acid and 1.27 g (0.011 mol) of N-hydroxysuccinimide were initially introduced into 30 ml of acetonitrile and the suspension was stirred at room temperature. This suspension was treated in the course of 10 min. with a solution of 2.53 g (0.025 mol) of triethylamine in 10 ml of acetonitrile and the mixture was stirred at room temperature for 30 min. A solution of 3.22 g (0.012 mol) of diphenyl chlorophosphate in 10 ml of acetonitrile was then added dropwise in the course of 10 min. The deep red-colored suspension obtained was stirred at room temperature for 20 hours. After ending of the reaction, the reaction mixture was evaporated in vacuo and the violet residue was taken up in 100 ml of dichloromethane. The organic phase was washed with 100 ml each of water, 1N hydrochloric acid and dil. $NaHCO_3$ solution. After evaporating the organic phase, 2.55 g of crude product were obtained. This was washed by stirring in 25 ml of ethanol for 2.5 hours. The residue was filtered off, washed with 4 ml of ethanol and dried in vacuo. 1.85 g (69%) of a violet solid of quinaldic acid succinimidyl ester were obtained.

M.p.: 190–194° C. (dec.)

EXAMPLE 7

1.73 g (0.010 mol) of quinaldic acid and 1.27 g (0.011 mol) of N-hydroxysuccinimide were initially introduced into 30 ml of acetone and 1.27 g (0.011 mol) of solid N-hydroxysuccinimide were added. This suspension was treated in the course of 5 min. with a solution of 2.48 g (0.025 mol) of 1-methyl-2-pyrrolidone in 10 ml of acetone and the mixture was stirred at room temperature for 30 min. A solution of 3.22 g (0.012 mol) of diphenyl chlorophosphate in 10 ml of acetone was then added dropwise. The suspension obtained was stirred at room temperature for 69 hours. After ending of the reaction, the yellowish reaction mixture was evaporated and the residue was taken up in 100 ml of dichloromethane and the organic phase was washed with 60 ml each of water, 2N hydrochloric acid, sat. $NaHCO_3$ solution and water again. After evaporating the organic phase, the residue which remained was washed by stirring in 20 ml of ethanol for 30 minutes, filtered off, washed with 3 ml of ethanol and dried for 4 hours at 10 mbar and 30° C. 0.95 g (35%) of a violet solid of quinaldic acid succinimidyl ester was obtained.

M.p.: 192–196° C. (dec.)

EXAMPLE 8

2.51 g (0.010 mol) of Z-valine were initially introduced into 30 ml of ethyl acetate and 1.27 g (0.011 mol) of solid N-hydroxysuccinimide were added. This suspension was treated with a solution of 2.53 g (0.025 mol) of triethylamine in 10 ml of ethyl acetate and the mixture was stirred at room temperature for 30 min. A solution of 3.22 g (0.012 mol) of diphenyl chlorophosphate in 10 ml of ethyl acetate was then added dropwise. A thick suspension was formed in this case with slight warming to 32° C. from the previously clear solution, which was stirred at room temperature for 23 hours and then filtered. The filter residue was washed twice with 10 ml each of ethyl acetate. The combined filtrates were washed with 25 ml each of water and 5% strength $NaHCO_3$ solution, and again with 2×25 ml of water. After phase separation, the ethyl acetate phase was dried over sodium sulfate and filtered, and the diluent was removed in vacuo. 3.25 g of a white solid were obtained. 2.98 g of this were reprecipitated from a mixture of 5 ml of dichloromethane and 15 ml of diisopropyl ether, whereupon 2.41 g (76%) of fine white crystals of Z-valine succinimidyl ester were obtained.

M.p.: 117–120° C.

EXAMPLE 9

5.99 g (0.020 mol) of Z-phenylalanine, 2.42 g (0.021 mol) of N-hydroxysuccinimide and 6.72 g (0.080 mol) of solid sodium hydrogencarbonate were initially introduced into 20 ml of ethyl acetate and the mixture was stirred at room temperature. A solution of 5.64 g (0.021 mol) of diphenyl chlorophosphate in 40 ml of ethyl acetate was then added dropwise in the course of 20 minutes, the suspension thickening. After dilution with 50 ml of ethyl acetate, the reaction mixture was warmed at 50° C. for 2 hours until no further reaction was found by means of TLC checking. The reaction mixture was washed with 50 ml each of water, sat. $NaHCO_3$ solution and again with water. After phase separation had taken place, the ethyl acetate phase was evaporated at 50° C. in vacuo. 4.81 g of crystalline crude product were obtained, which was washed by stirring with 20 ml of methyl tert-butyl ether at room temperature for 2 hours. The yield of Z-phenylalanine succinimidyl ester was 4.29 g (54%).

M.p.: 135–139° C.

EXAMPLE 10

1.07 g (0.0030 mol) of Z-aspartic acid β-benzyl ester were initially introduced into 10 ml of ethyl acetate and 0.38 g (0.0033 mol) of solid N-hydroxysuccinimide were added. A solution of 0.76 g (0.0075 mol) of triethylamine in ethyl acetate was then added to this suspension and it was stirred at room temperature for 10 minutes. A solution of 0.97 g (0.0075 mol) of diphenyl chlorophosphate in 3 ml of ethyl acetate was then added dropwise, whereby a thick suspension resulted from the previously clear solution with slight warming to at most 32° C. This was stirred at room temperature for 24 hours to complete the reaction and then filtered. The filter residue was washed twice with 3 ml of ethyl acetate each time. The combined filtrates were washed twice with 25 ml each of water and 5% strength $NaHCO_3$ solution and then again with 50 ml of water. After phase separation, the ethyl acetate phase was dried over sodium sulfate and filtered, and the diluent was removed in vacuo. 1.37 g of a colorless, resinous crude product were isolated and were washed by stirring with a mixture of 2.5 ml of dichloromethane and 25 ml of diisopropyl ether, and also 10 ml of hexane, and then crystallized by warming to 40° C. in 50 ml of diisopropyl ether. After filtering off, washing with 2×5 ml of diisopropyl ether and drying in vacuo, 0.98 g (72%) of white, crystalline Z-aspartic acid β-benzyl ester succinimidyl ester was obtained.

M.p.: 82–84° C.

EXAMPLE 11

0.72 g (0.010 mol) of acrylic acid was initially introduced into 30 ml of acetone and 1.27 g (0.011 mol) of solid N-hydroxysuccinimide were added. The resulting solution was treated with 3.36 g (0.040 mol) of solid sodium hydrogencarbonate and the white suspension thus obtained was stirred at room temperature. A solution of 3.22 g (0.012 mol) of diphenyl chlorophosphate in 10 ml of acetone was then added dropwise and the reaction mixture was stirred at room temperature for 24 hours and at 50° C. for a further 3 hours to complete the reaction, the thickening suspension being diluted with 25 ml of acetone. The diluent was then removed in vacuo and the residue was taken up in 60 ml of dichloromethane. Undissolved solid was filtered and washed twice with 10 ml each of dichloromethane. The combined dichloromethane phases were washed with 40 ml of water and, after phase separation, evaporated in vacuo. 1.53 g of solid crude product were obtained, which was washed by stirring with 15 ml of diisopropyl ether for 3 hours. The white solid which remained was filtered off, washed twice with 3 ml of diisopropyl ether each time and dried in vacuo. 1.1 g (65%) of acrylic acid succinimidyl ester were obtained.

M.p.: 63–68° C.

EXAMPLE 12

1.27 g (0.011 mol) of N-hydroxysuccinimide were initially introduced into 10 ml of ethyl acetate, a solution of 3.22 g (0.012 mol) of diphenyl chlorophosphate in 10 ml of ethyl acetate was added and then a solution of 2.53 g (0.025 mol) of triethylamine in 10 ml of ethyl acetate was added dropwise in the course of 10 minutes, the temperature rising to 41° C. A thick, white suspension resulted, which was treated with a solution of 0.6 g (0.01 mol) of acetic acid in 10 ml of ethyl acetate and heated at 45–55° C. for 16 hours. After ending of the reaction, the solid was filtered off and washed with 2×3 ml of ethyl acetate. The combined filtrates were evaporated in vacuo and the semi-crystalline residue which remained was washed by stirring with 20 ml of ethanol for 30 minutes. The white solid thus obtained was filtered off, washed with 2×3 ml of ethanol, sucked dry and then washed by stirring with 10 ml of isopropanol. After filtering off, washing with 2×2 ml of isopropanol and drying in vacuo, 1.1 g (70%) of white acetic acid succinimidyl eater were obtained.

M.p.: 130–134° C.

EXAMPLE 13

2.42 g (0.021 mol) of N-hydroxysuccinimide, 2.72 g (0.021 mol) of 4-toluic acid and 4.05 g (0.040 mol) of triethylamine were initially introduced into 20 ml of ethyl acetate and the suspension was stirred at room temperature. A solution of 5.64 g (0.021 mol) of diphenyl chlorophosphate in 40 ml of ethyl acetate was added dropwise to this suspension in the course of 20 minutes, the reaction mixture warming to about 35° C. To complete the reaction, it was stirred at room temperature for a further 1 hour. The reaction mixture was then diluted with 50 ml of ethyl acetate and washed with 50 ml each of water, 2N hydrochloric acid, saturated sodium hydrogencarbonate solution and water again. The organic phase was separated off and treated with 4.05 g (0.040 mol) of triethylamine and 2.62 g (0.020 mol) of L-valine methyl ester. The reaction mixture was stirred at room temperature for 1.5 hours and then heated under reflux for 3.5 hours. After stirring at room temperature overnight, an oily, heavier second phase was separated off and the ethyl acetate phase was washed with 50 ml each of water, sat. $NaHCO_3$ solution and a further three times with 50 ml each of water. After removing the diluent at 50° C. in vacuo, 3.41 g of crude product remained. 3.01 g of this were washed by stirring with 10 ml of methyl tertiary-butyl ether for 1 hour. After filtration and drying of the residue in vacuo at 50° C., 2.42 g (55%) of white, crystalline 4-toluic acid L-valine methyl ester amide were obtained.

M.p.: 98–100° C.

EXAMPLE 14

5.65 g (0.015 mol) of an ECPA-succinimidyl ester obtained according to Example 1 or 2 were dissolved in 45 ml of ethanol and treated in the course of 5 minutes with a solution of 3.4 g (0.029 mol) of L-proline in 5.65 ml of water and then in the course of 15 minutes with 8.3 ml (0.060 mol) of triethylamine. In the course of this the temperature rose from 22 to 30° C. The solution was then stirred at room temperature overnight and the ethanol was then removed in a rotary evaporator at 40° C. and 20 mbar. The residue was dissolved in 17 ml of water and then extracted 2 times with 55 ml each and once with 25 ml of methyl tertiary-butyl ether (MTBE). The 3 MTBE phases were combined and concentrated in a rotary evaporator at 40° C. and 20 mbar. The final weight was 0.90 g. The aqueous phase was adjusted to pH 2.8 using 6 ml of 2M sulfuric acid of pH 6.3. 1.7 g of sodium sulfate p.a. (0.7 mol based on $H_2O$) were then added. The mixture was then extracted three times with 80 ml each and twice with 30 ml each of ethyl acetate. The combined ethyl acetate phases were dried using sodium sulfate and concentrated in a rotary evaporator at 40° C. and 20 mbar. The final weight of (S,S,S)-N-((1-ethoxycarbonyl-3-phenylpropyl)alanyl)proline was 5.25 g (92.9%)

EXAMPLE 15

Analogous example 3 2,76 g (0.024 mol) of N-hydroxysuccinimide and 5.06 g (0,050 mol) of triethylamine were initially introduced into 5 ml of ethyl acetate and stirred at room temperature. 2.72 g (0.020 mol) of solid 4-toluic acid were added to this suspension in the course of 5 min. and then a solution of 3.47 g (0,020 mol) of diethyl chlorophosphate was added dropwise in the course of 20 min., the reaction mixture warming to about 35° C. The mixture was stirred at room temperature for 3 hours until the reaction was complete. The further proceeding was performed analogous example 3. 2.8 g of crude 4-toluic acid succinimidyl ester were isolated.

We claim:

1. A process for the preparation of reaction products of carboxylic acid succinimidyl esters, which comprises reacting N-hydroxy-succinimide with a carboxylic acid and a halophosphoric acid ester of the formula

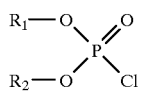

in which $R_1$ and $R_2$ are identical or different and are a $C_2$- to $C_6$-alkyl radical or a phenyl radical, or $R_1$ and $R_2$ together form a $C_6$-aryl radical, in the presence of a base in a diluent at a temperature of 0° C. up to 100° C., to form a reaction mixture which contains a carboxylic acid succinimidyl ester, and then reacting such reaction mixture with a nucleophile compound suitable for acylations.

2. The process as claimed in claim 1, wherein the carboxylic acid succinimidyl ester is coupled to the amino group of an amino acid or of an amino acid derivative with elimination of N-hydroxysuccinimide to give a peptide.

* * * * *